(12) United States Patent
Smith et al.

(10) Patent No.: US 6,989,399 B2
(45) Date of Patent: Jan. 24, 2006

(54) ANTIAMYLOID PHENYLSULFONAMIDES: N-ALKANOL DERIVATIVES

(75) Inventors: David W. Smith, Madison, CT (US); Michael F. Parker, Higganum, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 368 days.

(21) Appl. No.: 10/626,299

(22) Filed: Jul. 24, 2003

(65) Prior Publication Data

US 2004/0097572 A1    May 20, 2004

Related U.S. Application Data

(60) Provisional application No. 60/400,241, filed on Aug. 1, 2002.

(51) Int. Cl.
*A61K 31/4164*  (2006.01)
*C07D 233/54*   (2006.01)

(52) U.S. Cl. ........... 514/399; 548/300.1; 548/335.1; 548/335.5; 514/396

(58) Field of Classification Search ........... 548/300.1, 548/335.1, 335.5; 514/396, 399
See application file for complete search history.

(56) References Cited

U.S. PATENT DOCUMENTS 5,880,151 A * 3/1999 Medina et al. ............ 514/518
6,121,304 A * 9/2000 Flygare et al. ............ 514/403
6,448,290 B1 * 9/2002 Ohuchida et al. ......... 514/471

FOREIGN PATENT DOCUMENTS

EP        0815861 B1     9/2001
WO      WO 00/50391     8/2000

* cited by examiner

Primary Examiner—Golam M. M. Shameem
(74) Attorney, Agent, or Firm—James Epperson

(57) ABSTRACT

A series of N-alkanol-N-phenyl benzenesulfonamide and related derivatives of the Formula I are disclosed,

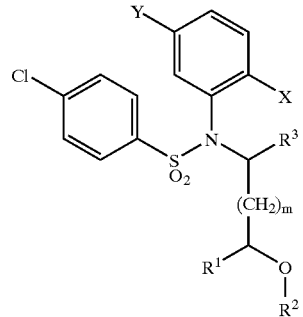

wherein $R^1$, $R^2$, $R^3$, X, and Y are defined herein. The compounds are inhibitors of β-amyloid peptide (β-AP) production and are useful in the treatment of Alzheimer's Disease and other conditions characterized by aberrant extracellular deposition of amyloid. Pharmaceutical compositions and methods of treatment are also disclosed.

6 Claims, No Drawings

ANTIAMYLOID PHENYLSULFONAMIDES: N-ALKANOL DERIVATIVES

CROSS-REFERENCE TO RELATED APPLICATIONS

This application claims the benefit of U.S. provisional application No. 60/400,241, filed Aug. 1, 2002.

BACKGROUND OF THE INVENTION

This invention provides novel benzenesulfonamide compounds having drug and bio-affecting properties, their pharmaceutical compositions, and method of use. In particular, the invention is concerned with N-alkanol derivatives of N-phenyl-benzenesulfonamides. These compounds uniquely inhibit β-amyloid peptide (β-AP) production, thereby acting to prevent the accumulation of amyloid protein deposits in the brain. More particularly, the present invention relates to the treatment of Alzheimer's Disease (AD).

1. Field of the Invention

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (greater than $100 billion annually in the U.S.) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. There is currently no effective treatment.

There have been many theories relating to the etiology and pathogenesis of AD. These theories were either based on analogies with other diseases and conditions (e.g., slow virus and aluminum theories), or based on pathologic observations (e.g., cholinergic, amyloid, or tangle theories). Genetic analysis can potentially differentiate between competing theories. The identification of mutations in the β-amyloid precursor protein (β-APP) of individuals prone to early onset forms of AD and related disorders strongly supports the amyloidogenic theories.

The β-amyloid precursor protein (β-APP), a large membrane spanning glycoprotein found in tissues of mammals, including humans, is encoded by a gene on the long arm of human chromosome 21. The main constituent of the plaques, tangles and amyloid deposits is known to be β-amyloid peptides (β-AP), composed of approximately 39 to 43 amino acid fragments of β-APP, and in particular, the 40 amino acid fragment known as Aβ1-40. Several lines of evidence support the involvement of β-AP in the pathogenesis of AD lesions. β-AP and related fragments have been shown to be toxic for PC-12 cell lines and primary cultures of neurons, as well as causing neuronal degeneration with accompanying amnesia in rodents. Strong evidence for the role of β-AP in AD consists of observations of genetic β-APP mutations in individuals with certain forms of Familial Alzheimer's Disease (FAD) and the correlation of disease onset with altered release of β-AP fragments.

It is presently believed that the development of amyloid plaques in the brains of AD patients is a result of excess production and/or reduced clearance or removal of β-AP. It is known that a basal level of β-AP production may be a normal process and that multiple pathways for cleavage of β-APP exist. Currently, however, it is unclear which classes of proteinases or inhibitors thereof that would be effective in treating AD. Various peptidergic compounds and their pharmaceutical compositions have been disclosed as useful in inhibiting or preventing amyloid protein deposits in brains of AD and Down's Syndrome patients.

2. Description of Related Art

Bös, et al. in EP application 815861A1 disclosed a series of sulfonamides shown below having selective affinity for the 5-HT$_6$ receptor. Among the uses given for these compounds is use in Alzheimer's disease.

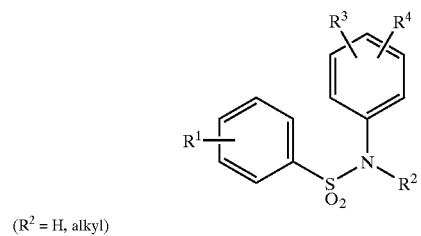

($R^2$ = H, alkyl)

Smith, et al. in WO 00/50391, published Aug. 31, 2000, have disclosed a series of sulfonamide compounds that can act to modulate production of amyloid β protein as a means of treating a variety of diseases, especially Alzheimer's Disease and other diseases relating to the deposition of amyloid.

Nothing in these references discloses or suggests the novel compounds of this invention or their use as inhibitors of β-AP production.

SUMMARY OF THE INVENTION

A series of N-alkanol and related derivatives of N-phenyl-benzenesulfonamides of Formula I is disclosed. These compounds inhibit the production of β-amyloid peptide (β-AP) from β-amyloid precursor protein (β-APP). The pharmacologic action of these compounds makes them useful for treating conditions responsive to the inhibition of β-AP in a patient, for example, Alzheimer's Disease (AD) and Down's Syndrome. Pharmaceutical compositions and methods of treatment are also disclosed.

DETAILED DESCRIPTION OF THE INVENTION

The present invention comprises compounds of Formula I, their pharmaceutical formulations, and their use in inhibiting β-AP production in patients suffering from or susceptible to AD or other disorders resulting from β-AP accumulation in brain tissue. The compounds of Formula I include all stereoisomers, pharmaceutically acceptable salts, and solvates including hydrates thereof having the following formula and meanings.

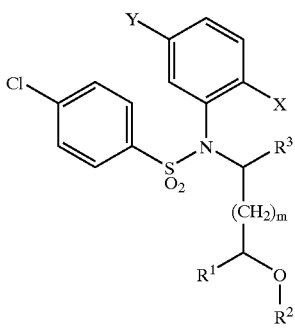

where
X and Y are independently selected from halogen, hydroxymethyl, and acetoxymethyl;
$R^1$ is selected from $C_{1-6}$alkyl, $C_{3-6}$alkenyl, $C_{3-6}$alkynyl, $C_{3-7}$cycloalkyl, $C_{5-7}$cycloalkenyl, $-(CH_2)_{1-6}CO_2R^3$, and

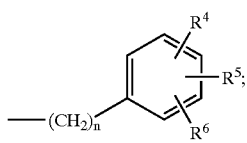

$R^2$ is selected from hydrogen, $C_{1-6}$alkylcarbonyl, $C_{3-7}$cycloalkylcarbonyl, $CONHR^3$ and

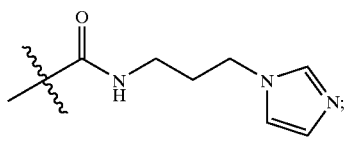

$R^3$ is selected from hydrogen and $C_{1-6}$alkyl;
$R^4$, $R^5$, and $R^6$ are independently selected from hydrogen, $C_{1-6}$alkyl, and $C_{1-6}$alkoxy;
m is 0 or an integer from 1 to 6; and
n is 0 or an integer from 1 to 6.

As the compounds of the present invention possess asymmetric carbon atoms, the present invention includes all stereomeric forms of the compounds of Formula I as described herein and in the claims. The use of a single designation such as (R) or (S) is intended to include mostly one stereoisomer. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The possible enantiomeric forms may also be separated by fractionation through chiral high pressure liquid chromatography columns.

The invention includes all pharmaceutically acceptable salt forms of the instant compounds. Pharmaceutically acceptable salts are those in which the counter ions do not contribute significantly to the physiological activity or toxicity of the compounds and as such function as pharmacological equivalents. In many instances, salts have physical properties that make them desirable for formulation, such as solubility or crystallinity. The salts can be made according to common organic techniques employing commercially available reagents. Suitable anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Suitable cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the instant compounds. Solvates do not contribute significantly to the physiological activity or toxicity of the compounds and as such function as pharmacological equivalents. Solvates may form in stoichiometric amounts or may form with adventitious solvent or a combination of both. One type of solvate is hydrate and some hydrated forms include monohydrate, hemihydrate, and dihydrate.

One group of preferred compounds are Formula I compounds where $R^3$ is $C_{1-6}$alkyl and where the carbon to which $R^3$ is attached is of the (R) configuration as shown in the structure below.

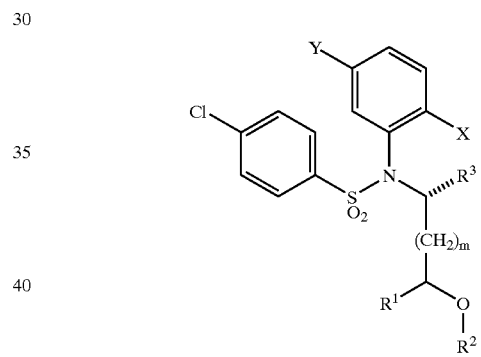

Another group of preferred compounds are Formula I compounds where $R^1$ is $C_{1-6}$alkyl, $C_{3-6}$alkenyl, or $C_{3-6}$alkynyl.

In the method of the present invention, the term "therapeutically effective amount" means the total amount of each active component of the method that is sufficient to show a meaningful patient benefit, i.e., improve one or more clinical parameters of disease activity, e.g. retention or cognition; or improve disease symptoms such as anxiety or neuromotor control. The subject amount is further characterized by inhibition of β-amyloid peptide production as determined using in vitro assays or in vivo animal models of disease. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means ameliorating one or more clinical indicia of disease activity in a patient having a disease associated with β-amyloid peptide.

The compounds of the present invention may be produced by the process shown in Scheme 1. Compounds of Formula IV can be prepared by reacting an appropriately substituted aniline with 4-chlorobenzenesulfonylchloride and are known in the literature. Formula IV compounds undergo Mitsunobu-type reactions with various alcohols including those of Formulas Va and Vb (where PG is a commonly used protecting group). By employing these or other alcohols, Formula IIIa and IIIb compounds can be produced. These intermediates can be transformed into compounds of Formula II by methods well known to those skilled in organic synthesis. For example, a Formula IV compound can be coupled with methyl lactate to produce a Formula IIIa compound. The ester moiety of this compound can be reduced to an aldehyde to give a compound of Formula II. Another example would be to couple a Formula IV compound with 3-trityloxy-2-butanol, remove the trityl moiety, and oxidize the resultant alcohol to give a Formula II compound. Formula II compounds, in turn, can be reacted with a variety of carbon nucleophiles, including organometallic compounds, to generate Formula I compounds. Certain Formula I compounds may be further transformed into additional examples of Formula I by common methods in organic chemistry. For example, a Formula I compound where $R^2$ is H can be acylated with a variety of agents including acid chlorides, chloroformates, and isocyanates. More examples of these transformations will be given in the Specific Embodiments section and will provide additional experimental detail.

(2000); Zhang et al., *Biochemistry*, 40, p. 5049-5055 (2001)). An isolated membrane fraction can be prepared from human derived cell lines such as HeLa and H4 which have been transfected with wild type or mutant forms of β-APP or a human alkaline phosphatase β-APP fusion construct, and stably express high levels of γ-secretase substrates. The endogenous γ-secretase present in the isolated membranes prepared at 0–4 degrees C. cleaves the β-APP substrates when the membranes are shifted from 0–4 to 37 degrees C. Detection of the cleavage products including Aβ can be monitored by standard techniques such as immunoprecipitation (Citron et al., *Proc. Natl. Acad. Sci. USA*, 93, p. 13170–13175), western blot (Klafki et al., *J. Biol. Chem.* 271, p. 28655–28659), enzyme linked immunosorbent assay (ELISA) as demonstrated by Seubert et al., *Nature*, 359, p. 325–327 (1992), or by a preferred method using time-resolved fluorescence of the homogeneous sample containing membranes and Aβ (Roberts et al., WO 01/75435; Shearman et al., *Biochemistry*, 39, p. 8698–8704 (2000)). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the γ-secretase cleavage. The second antibody binds to any other epitope present on Aβ. For example,

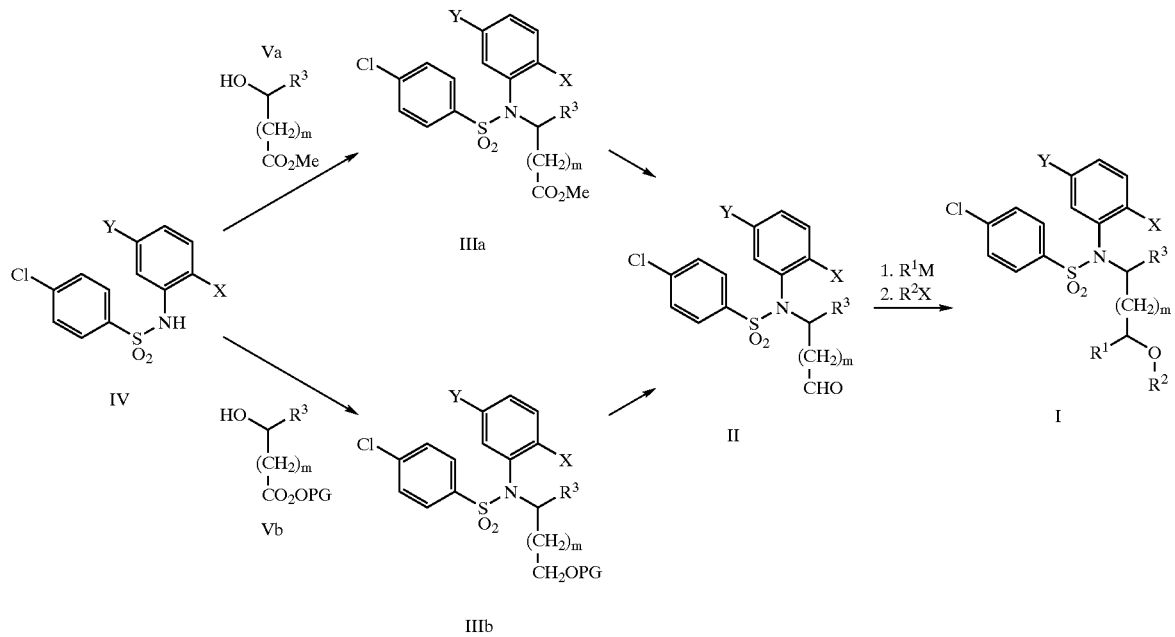

Scheme 1.

Biological Activity: Detection of γ-Secretase Cleavage and Aβ Production

The detection of γ-secretase activity requires assays capable of reliable, accurate and expedient detection of γ-secretase cleavage products, particularly Aβ. An isolated membrane fraction that contains functionally active γ-secretase and β-APP substrates can generate γ-secretase cleavage products including Aβ (Roberts et al., WO 01/75435; Fechteler et al., Patent Application No. DE 99-19941039 19990828; Shearman et al., *Biochemistry*, 39, p. 8698–8704 antibodies that bind the N-terminal region (e.g., 26D6-B2-B3® SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of γ-secretase. The isolated membrane assay can be used to identify candidate agents that inhibit the activity of γ-secretase cleavage and Aβ production.

A typical membrane-based assay requires 45 µg membrane protein per well in a 96- or 384-well format. Membranes in a neutral buffer are combined with the test compound and shifted from 0–4 to 37 degrees C. Test agents may typically consist of synthetic compounds, secondary metabolites from bacterial or fungal fermentation extracts, or extracts from plant or marine samples. All synthetic agents are initially screened at doses ranging from 10–100 µM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts et al., WO 01/75435; Shearman et al., Biochemistry, 39, p. 8698–8704 (2000)). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. If a compound is found to be active then a dose response experiment is performed to determine the lowest dose of compound necessary to elicit the inhibition of the production of Aβ.

The Formula I compounds were tested in the assay described above and found to be active as inhibitors of γ-secretase. The level of inhibition measured by $IC_{50}$ values found that the compounds of formula I have $IC_{50}$ values lower than 5 µM. The results obtained when the invention compounds are subjected to the above described assay are summarized in Table 1. In the table, an inhibitory concentration ($IC_{50}$) of less than or equal to 50 nM is represented by +++; between 50 nM and 200 nM by ++; between 200 nM and 5000 nM by +. Preferred compounds have an $IC_{50}$ less than 100 nM and most preferred compounds have an $IC_{50}$ less than 50 nM.

TABLE 1

Inhibition of β-Amyloid Peptide by Representative Formula I Compounds.

| Example | Activity |
| --- | --- |
| 5A | ++ |
| 5B | + |
| 6A | ++ |
| 6B | + |
| 7 | ++ |
| 8 | ++ |
| 9A | ++ |
| 9B | ++ |
| 10 | + |
| 11 | + |
| 12 | + |
| 13 | + |
| 14 | + |
| 15A | +++ |
| 15 | +++ |
| 16A | + |
| 17A | + |
| 17B | + |
| 18A | ++ |
| 18B | + |
| 19A | ++ |
| 19B | ++ |
| 20A | ++ |
| 20B | + |
| 21A | +++ |
| 21B | +++ |
| 22 | + |
| 23A | +++ |
| 24 | ++ |
| 25A | ++ |
| 26A | +++ |
| 27A | +++ |
| 28 | ++ |
| 29 | ++ |
| 30 | ++ |

Activity: $IC_{50}$ 200–5000 nM = +; <200 nM = ++; <50 nM = +++.

Therefore, the compounds of Formula I or pharmaceutical compositions thereof are useful in the treatment of disorders associated with the inhibition of β-amyloid peptide.

Accumulating findings have led to the perception that compounds that inhibit the formation of β-AP from β-APP would be clinically efficacious in treating disorders such as Alzheimer's Disease, Down's Syndrome, and certain forms of brain degeneration. In this regard, certain compounds of the instant invention when administered orally or intravenously to experimental animals were capable of entering the CNS and inhibiting production of β-AP formation in experimental animal models of disease.

In another embodiment, this invention includes pharmaceutical compositions comprising at least one compound of Formula I in combination with a pharmaceutical adjuvant, carrier or diluent.

In still another embodiment, this invention relates to a method of treatment of disorders characterized by aberrant extracellular deposition of amyloid and which are responsive to the inhibition of β-amyloid peptide in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating systemic (vascular) amyloidosis, pulmonary or muscle amyloidosis, Alzheimer's Disease, Down's Syndrome, or other diseases characterized by extracellular amyloid deposition in a mammal in need thereof, which comprises administering to said mammal a therapeutically effective amount of a compound of Formula I or a nontoxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of β-AP inhibition desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to aberrant production and/or extracellular deposition of β-AP as described herein, generally the daily dose will be from about 0.05 mg/kg to about 10 mg/kg and preferably, about 0.1 to 2 mg/kg when administered parenterally. For oral administration, the dose may be in the range from about 1 to about 50 mg/kg and preferably from 0.1 to 2 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the meaning of the invention.

DESCRIPTON OF SPECIFIC EMBODIMENTS

In the following examples, all temperatures are given in degrees Centigrade. Melting points were recorded on a Gallenkamp capillary melting point apparatus and are uncorrected. Proton magnetic resonance ($^1$H NMR) spectra were recorded on a Bruker AC 300. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) or sodium chloride film were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations $[\alpha]_D^{25}$ were determined on a Perkin-Elmer 41 polarimeter in the solvents indicated. Low resolution mass spectra (MS) and the apparent molecular (MH$^+$) or (M–H)$^+$ was determined on a Finnigan TSQ 7000. The elemental analysis are reported as percent by weight.

Synthesis of Formula III Intermediates

EXAMPLE 1

2-[((4-Chloro-benzenesulfonyl)-(2,5-dichlorophenyl)-(1R)-amino]propionic acid methyl ester A solution of N-(2,5-dichlorophenyl)-4-chlorobenzenesulfonamide (10 g, 30 mmol), methyl (S)-lactate (10.7 g, 45 mmol), and triphenylphosphine (11.8 g, 45 mmol) in THF (200 mL) at 0° C. was added diethyl azodicarboxylate (7.8 g, 45 mmol). The reaction was allowed to warm to ambient temperature with stirring for 18 h. The reaction was then diluted with EtOAc and washed with H$_2$O, 1N HCl, and brine. The organic phase was dried over MgSO$_4$, filtered, and concentrated in vacuo. The resulting solid was further purified by silica gel chromatography (15% EtOAc/hexanes) to afford 12.46 g of the title compound as a white solid (97% yield): $^1$H NMR (DMSO-d$_6$) δ 7.82 (d, 2H, J=8.0 Hz), 7.64 (d, 2H, J=8.0 Hz), 7.42 (s, br, 1H) 6.99 (s, 1H), 4.25 (m, 1H), 3.51–3.60 (s, br, 4H), 3.18–3.41 (m, 2H), 2.25–2.35 (s, br, 4H), 2.27 (m, 2H) 1.15–1.62 (m, 9H), 0.80 (d, 6H, J=6.0 Hz).

EXAMPLE 2

4-Chloro-N-(2,5-dichloro-phenyl)-N-(1R)-(1-methyl-4-trityloxybutyl)benzenesulfonamide To N-(2,5-dichlorophenyl)-4-chlorobenzenesulfonamide (5.0 g, 15 mmol), (S) -4-trityloxy-butan-2-ol (7.7 g, 22 mmol), and triphenylphosphine (5.8 g, 22 mmol) in THF (200 mL) at 0° C. was added diethyl azodicarboxylate (3.8 g, 22 mmol). The reaction was allowed to warm to ambient temperature with stirring 18 h The reaction was then diluted with EtOAc and washed with H$_2$O, 1N HCl, and brine. The organic phase was dried over MgSO$_4$, filtered, and concentrated in vacuo. Silica gel chromatography (15% EtOAc/hexanes) of the concentrate afforded the title compound as a white solid (5.25 g, 55% yield).

Synthesis of Formula II Intermediates

EXAMPLE 3

4-Chloro-N-(2,5-dichlorophenyl)-N-(1R)-(1-methyl-2-oxoethyl)benzenesulfonamide To a solution of LAH (18.5 mL of a 1M solution in THF, 18.5 mmol) in THF (50 mL) at −78° C. was added dropwise a solution of N-(2,5-dichlorophenyl)-N-(1-carbomethoxyprop-2-yl)-4-chlorobenzenesulfonamide (6.5 g, 15.4 mmol) in THF (100 mL). After the addition was complete, the reaction was briefly allowed to warm to 0° C. followed by cooling to −78° C. The suspension was quenched with 0.5N HCl (20 mL) and stirred at room temperature for 3 h. The resulting precipitate was removed by filteration and the filter cake washed well with $Et_2O$. The filtrate was dried over $MgSO_4$ and concentrated in vacuo to afford 4-chloro-N-(2,5-dichlorophenyl)-N-(1R)-(2-hydroxy-1-methylethyl)benzenesulfonamide as a white wax (5.88 g, 98% yield): $^1$H NMR ($CDCl_3$) δ 7.77 (d, 2H, J=7.0 Hz), 7.34–7.52 (m, 5H), 4.27–4.42 (m, 1H), 3.35–3.61 (m, 2H), 1.77 (s, br, 1H), 1.05–1.09 (m, 3H).

To a solution of (Dess-Martin periodinane) (7.0 g, 16.5 mmol) in dichloromethane (150 mL) was added a solution of 4-chloro-N-(2,5-dichlorophenyl)-N-( 1R)(2-hydroxy-1-methylethyl) (5.88 g, 15 mmol) in dichloromethane (50 mL) dropwise at 0° C. The reaction was allowed to slowly come to room temperature with stirring over 18 h. The reaction was then quenched with a saturated solution of 1:1 $NaHCO_3$/$NaHSO_3$ (25 mL), diluted with EtOAc, and washed with $H_2O$ and brine. The organic extract was dried over $MgSO_4$, filtered, and concentrated in vacuo. Flash silica gel chromatography (silica gel, 15% EtOAc/hexanes) of the concentrate afforded the title compound as a white wax (4.5 g, 78% yield): $^1$H NMR ($CDCl_3$) δ 9.87 (d, rotomers, 1H), 7.68 (d, 2H, J=8.0 Hz), 7.33–7.55 (m, 5H), 4.35–4.42 (m, 1H), 1.17–1.36 (m, 3H).

EXAMPLE 4

4-Chloro-N-(2,5-dichlorophenyl)-N-(1R)(1-methyl-4-oxobutyl)benzenesulfonamide 4-Chloro-N-(2,5-dichlorophenyl)-N-(1R)(1-methyl-4-trityloxybutyl)benzenesulfonamide (5.25 g, 8.0 mmol) was treated with amberlyst 15 (excess, 50 g) in MeOH (150 mL) at room temperature. After 18 h the amberlyst was removed by filtration and the filtrate was concentrated in vacuo. Silica gel chromatography (20% EtOAc/hexanes) of the concentrate afforded 4-chloro-N-(2,5-dichlorophenyl)-N-(1R)(4-hydroxy-1-methylbutyl)benzenesulfonamide (3.75 g, 63% yield): $^1$H NMR ($CDCl_3$) δ 7.74 (d, 2H, J=8.2 Hz), 7.34–7.52 (m, 5H), 4.18–4.41 (m, 1H), 3.35–3.61 (m, 2H), 1.61–1.72 (m, 2H), 1.77 (s, br, 1H), 1.05–1.09 (m, 3H)

To a solution of Dess-Martin periodinane (4.24 g, 10.0 mmol) in dichloromethane (100 mL) at 0° C. was added dropwise 4-chloro-N-(2,5-dichlorophenyl)-N-(1R)(4-hydroxy-1-methylbutyl)benzenesulfonamide (3.60 g, 8.8 mmol) in dichloromethane (50 mL). The reaction was allowed to slowly come to room temperature with stirring over 18 h. The reaction was then quenched with a saturated solution of 1:1 $NaHCO_3$/$NaHSO_3$ (25 mL) and diluted with EtOAc. The organic phase was washed with $H_2O$ and brine, dried over $MgSO_4$, filtered, and concentrated in vacuo. Flash silica gel chromatography (silica gel, 20% EtOAc/hexanes) of the concentrate afforded the title compound as a white wax (1.85 g, 51% yield): $^1$H NMR ($CDCl_3$) δ 9.70 (s, 1H), 7.68–7.75 (m, 2H), 6.98–7.49 (m, 5H), 4.80–4.85 (m, 1H), 2.36–3.00 (m, 2H), 1.17–1.36 (m, 3H).

Synthesis of Formula I Compounds

EXAMPLE 5

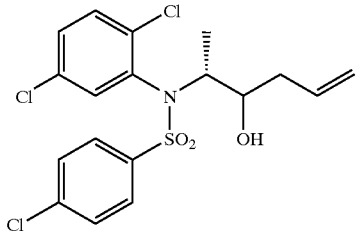

4-Chloro-N-(2,5-dichlorophenyl)-N-(1R)-(2-hydroxy-1-methylpent-4-enyl)-benzenesulfonamide (Isomers A and B)

Allylmagnesium bromide (7.2 mL of a 1M solution in $Et_2O$, 7.2 mmol) was added dropwise to a solution of 4-chloro-N-(2,5-dichlorophenyl)-N-(1R)(1-methyl-2-oxoethyl)benzenesulfonamide (1.4 g, 3.6 mmol) in THF (50 mL) at −78° C. After the addition was complete the reaction was maintained at −78° C. for 30 min and then allowed to warm to room temperature (approx. 1 h). The reaction was quenched with the addition of saturated $NaHCO_3$ and extracted with EtOAc. The combined organic extracts were washed with brine, dried over $K_2CO_3$, filtered, and concentrated in vacuo. Silica gel chromatography (10% EtOAc/hexanes) of the concentrate afford both diastereomers identified as isomer A (350 mg, 1$^{st}$ band to elute) as a clear wax and isomer B (750 mg, 2$^{nd}$ band to elute) (See Table 2 for NMR data).

EXAMPLE 6

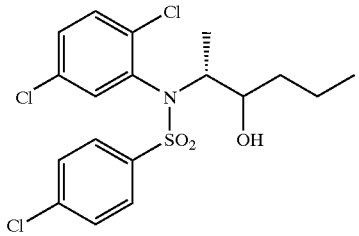

4-Chloro-N-(2,5-dichlorophenyl)-N-(1R)-(2-hydroxy-1-methylpentyl)benzenesulfonamide (Isomer A)

A suspension of 4-chloro-N-(2,5-dichlorophenyl)-N-(1R) (2-hydroxy-1-methylpent-4-enyl)benzenesulfonamide (150 mg, 0.3 mmol) and sulfided platinum (5 wt. % on carbon, 50 mg) in EtOH (50 mL) was hydrogenated at 45 psi for 3 h. The suspension was filtered through celite and concentrated in vacuo. Silica gel chromatography (10% EtOAc/hexanes)

of the concentrate afforded the title compound as a clear wax (120 mg, 80% yield): MS (ESI): (M−H)⁻436.34; [α]$_D$=−15.3° (c 1.00, MeOH), $^1$H NMR (DMSO-d$_6$) δ 7.81 (d, 2H, J=7.0 Hz), 7.60 (d, 2H,) J=7.0 Hz), 7.50 (s, br, 1H), 7.41 (d, 2H, J=8.0 Hz), 7.32 (m, 2H), 7.24 (m, 1H), 7.18 (s, br, 1H), 4.76 (dd, 2H, J=50 Hz, 15 Hz), 4.36 (t, 1H, J=7.0 Hz), 3.33 (s, 3H), 1.20–1.34 (m, 3H), 0.79 (d, 3H, J=6.0 Hz), 0.46 (d, 3H, J=6.0 Hz).

EXAMPLE 7

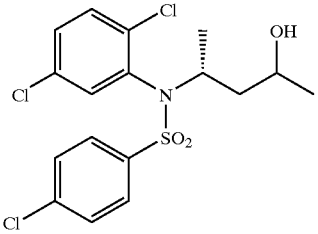

4-Chloro-N-(2,5-dichlorophenyl)-N-(1R)(2-hydroxy-1-methylbutyl)benzenesulfonamide Methylmagnesium bromide (0.4 mL of a 3M solution in THF, 1.2 mmol) was added dropwise to a −55° C. solution of 4-chloro-N-(2,5-dichlorophenyl)-N-(1R)(1-methyl-4-oxobutyl)benzenes (243 mg, 0.60 mmol) in THF (10 mL). After the addition was complete the reaction was maintained at −55° C. for 30 min followed by warming to room temperature (approx. 1 h). The reaction was quenched with the addition of saturated NaHCO$_3$ and extracted with EtOAc. The organic extracts were combined, washed with brine, dried over K$_2$CO$_3$, filtered, and concentrated in vacuo. Silica gel chromatography (10% EtOAc/hexanes) of the concentrate afforded 119 mg of a mixture of diastereomers as a clear wax: MS (ESI), (M−H)-422.07, $^1$H NMR (CDCl$_3$) δ 7.71–7.80 (m, 2H), 7.31–7.51 (m, 4H), 7.12 (d, 0.5H, J=2.4 Hz), 7.22(d, 0.5H, J=2.4 Hz), 4.40–4.56 (m, 1H), 3.71–4.11 (m, 1H), 1.72 (s, br, 1H), 1.11–1.50 (m, 8H).

EXAMPLE 8

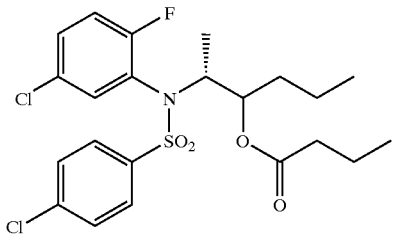

Butanoic Acid, 1-[(1R)-1-[1-[(5-chloro-2-fluorophenyl)[(4-chlorophenyl)sulfonyl]amino]ethyl]butyl ester (Isomer A)

To dichloromethane (20 mL) at room temperature was added 4-chloro-N-(2-fluoro-5-chlorophenyl)-N-(1R)-(2-hydroxy-1-methylpentyl)benzenesulfonamide (isomer A, 100 mg, 0.24 mmol), triethylamine (0.1 mL, 0.5 mmol), 4-(dimethylamino)pyridine (10 mg, 0.08 mmol), and butyric anhydride (48 mg, 0.3 mmol). After 48 h the reaction was diluted with dichloromethane and washed with 1N HCl, H$_2$O, and brine. The organic phase was dried over MgSO$_4$, filtered, and concentrated in vacuo. Silica gel chromatography (10% EtOAc/hexanes) of the concentrate afforded the title compound as a white wax (110 mg, 94% yield): $^1$H NMR (CDCl$_3$) δ 7.69 (d, 2H, J=8.0 Hz), 7.44 (d, 2H, J=8.0 Hz), 7.31–7.35 (m, 1H), 6.99–7.18 (m, 2H), 4.79–4.81 (m, 1H), 4.46–4.53 (m, 1H), 3.11–3.27 (m, 2H), 1.26–1.66 (m, 6H), 1.13 (d, 3H, J=6.6 Hz), 0.83–0.95 (m, 6H).

As can be seen from the above examples, Formula compounds can be generated from appropriate Formula III and nucleophilic reagents. Modifications to these processes would be known to skilled chemists. Formula I compounds are listed in Table 2.

TABLE 2

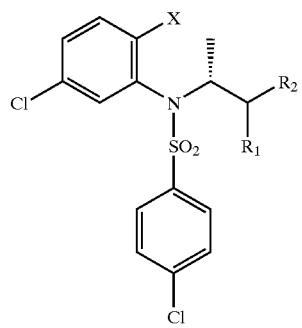

| Example | R$^1$ | R$^2$ | X | Isomer | Appearance | MF | Elemental Calcd. |
|---|---|---|---|---|---|---|---|
| 5 | OH | ⁓⧸= | Cl | A | Clear Wax | C$_{18}$H$_{18}$C$_{13}$NO$_3$S | C = 49.73<br>H = 4.17<br>N = 3.22 |
| 5 | OH | ⁓⧸= | Cl | B | Clear Wax | C$_{18}$H$_{18}$C$_{13}$NO$_3$S | C = 49.73<br>H = 4.17<br>N = 3.22 |

TABLE 2-continued

| | | | | | | | |
|---|---|---|---|---|---|---|---|
| 6 | OH |  | Cl | A | Clear Wax | $C_{18}H_{20}Cl_3NO_3S$ | C = 49.50<br>H = 4.62<br>N = 3.21 |
| 6 | OH | 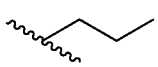 | Cl | B | Clear Wax | $C_{18}H_{20}Cl_3NO_3S$ | C = 49.50<br>H = 4.62<br>N = 3.21 |
| 7 | H | 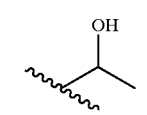 | Cl | Mixture | Wax | $C_{17}H_{18}Cl_3NO_3S$ | C = 48.30<br>H = 4.29<br>N = 3.31 |
| 8 | 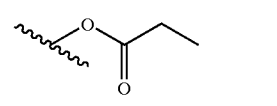 |  | F | A | Wax | $C_{22}H_{26}Cl_2FNO_4S$ | C = 53.88<br>H = 5.43<br>N = 2.76 |
| 9 | OH |  | Cl | A | Clear Wax | $C_{16}H_{16}Cl_3NO_3S$ | C = 47.02<br>H = 3.95<br>N = 3.43 |
| 9 | OH | 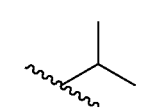 | Cl | B | White Solid | $C_{16}H_{16}Cl_3NO_3S$ | C = 47.02<br>H = 3.95<br>N = 3.43 |
| 10 | OH | 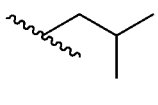 | Cl | Mixture | Clear Wax | $C_{18}H_{20}Cl_3NO_3S$ | H = 49.50<br>H = 4.62<br>N = 3.21 |
| 11 | OH |  | Cl | Mixture | Clear Wax | $C_{19}H_{22}Cl_3NO_3S$ | C = 50.62<br>H = 4.92<br>N = 3.11 |
| 12 | OH | 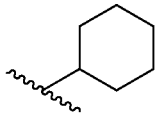 | Cl | Mixture | Oil | $C_{20}H_{22}Cl_3NO_3S$ | HPLC Purity[1] |
| 13 | OH | 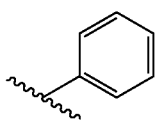 | Cl | Mixture | Wax | $C_{21}H_{24}Cl_3NO_3S \cdot$ 0.2 $CH_2Cl_2$ | C = 51.56<br>H = 4.98<br>N = 2.84 |
| 14 | OH |  | Cl | Mixture | White Wax | $C_{21}H_{18}Cl_3NO_3S \cdot$ 0.5 EtOAc | C = 53.66<br>H = 4.31<br>N = 2.72 |
| 15 | OH | 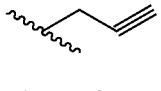 | Cl | A | Oil | $C_{18}H_{16}Cl_3NO_3S$ | HPLC Purity[1] |
| 15 | OH | 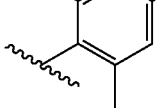 | Cl | Mixture | Wax | $C_{18}H_{16}Cl_3NO_3S$ | C = 49.46<br>H = 3.73<br>N = 3.24 |
| 16 | OH | 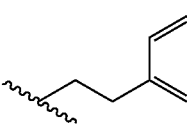 | Cl | A | White Solid | $C_{24}H_{24}Cl_3NO_3S$ | HPLC Purity[1] |
| 17 | OH |  | Cl | A | White Wax | $C_{23}H_{22}Cl_3NO_3S$ | HPLC Purity |

TABLE 2-continued

| # | R1 | R2 | X | A/B | Form | Formula | Analysis |
|---|---|---|---|---|---|---|---|
| 17 | OH | phenylpropyl | Cl | B | Wax | C₂₃H₂₂Cl₃NO₃S | C = 55.38, H = 4.45, N = 2.81 |
| 18 | OH | but-3-enyl | Cl | A | Wax | C₁₉H₂₀Cl₃NO₃S | C = 50.85, H = 4.49, N = 3.12 |
| 18 | OH | but-3-enyl | Cl | B | Wax | C₁₉H₂₀Cl₃NO₃S | C = 50.85, H = 4.49, N = 3.12 |
| 19 | OH | isopropyl | F | A | Wax | C₁₆H₁₆Cl₂FNO₃S | C = 48.99, H = 4.11, N = 3.69 |
| 19 | OH | isopropyl | F | B | Wax | C₁₆H₁₆Cl₂FNO₃S | C = 48.99, H = 4.11, N = 3.57 |
| 20 | OH | pentenyl | F | A | Oil | C₁₉H₂₀Cl₂FNO₃S | HPLC Purity[1] |
| 20 | OH | pentenyl | F | B | Wax | C₁₉H₂₀Cl₂FNO₃S | C = 52.79, H = 4.66, N = 3.24 |
| 21 | OH | butynyl | F | A* | Wax | C₁₈H₁₆Cl₂FNO₃S | C = 51.93, H = 3.87, N = 3.36 |
| 21 | OH | butynyl | F | B | Wax | C₁₈H₁₆Cl₂FNO₃S | HPLC Purity[1] |
| 22 | OH | 4-methoxybenzyl | F | Mixture | Wax | C₂₂H₂OCl₂FNO₄S · 0.25 EtOAc | C = 54.55, H = 4.38, N = 2.77 |
| 23 | OH | allyl-CH₂ | F | A | Clear Wax | C₁₈H₁₈Cl₂FNO₃S | C = 51.68, H = 4.34, N = 3.35 |
| 24 | OH | CH₂COOH | F | Mixture | White Solid | C₁₇H₁₆Cl₂FNO₅S · 0.9 H₂O | C = 45.12, H = 3.97, N = 3.10 |
| 25 | OC(O)CH(CH₃)₂ | butyl | F | A | Wax | C₂₄H₂₈Cl₂FNO₄S | C = 55.82, H = 5.46, N = 2.71 |
| 26 | CH₃ | OC(O)NH—(CH₂)₃-Imd | CH₂OH | A | Solid, mp 115° C. | | |
| 27 | OH | propyl | F | A | Clear Wax | C₁₈H₂OCl₂FNO₃S | C = 51.44, H = 4.80, N = 3.33 |
| 28 | H | 2-hydroxy-4-methylpentyl | Cl | Mixture | Wax | C₂₀H₂₄Cl₃NO₃S | HPLC Purity[1] |
| 29 | H | 2-hydroxy-pent-4-enyl | Cl | Mixture | Oil | C₂₀H₂₂Cl₃NO₃S | C = 51.90, H = 4.79, N = 3.03 |

TABLE 2-continued

| 30 | H | 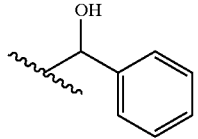 | Cl | Mixture | Wax | $C_{22}H_{20}Cl_3NO_3S$ | C = 54.50<br>H = 4.16<br>N = 2.89 |
|----|---|---|----|---------|-----|------------------------|-----------------------------------|

| Example | Analysis Found | NMR Data |
|---------|----------------|----------|
| 5 | C = 50.02<br>H = 4.51<br>N = 3.10 | $^1$H NMR (CDCl$_3$) δ 7.67–7.73 (m, 2H), 7.18–7.51 (m, 5H), 5.80–5.91 (m, 1H), 5.09–5.24 (m, 2H), 3.98–4.13 (m, 1H), 3.57–3.61 (m, 0.5H), 3.27–3.34 (m, 0.5H), 2.03–2.39 (m, 3H), 1.10–1.25 (m, 3H). |
| 5 | C = 50.00<br>H = 4.12<br>N = 3.09 | $^1$H NMR (CDCl$_3$) δ 7.64–7.71 (m, 2H), 7.30–7.51 (m, 4H), 7.04 (d, 1H, J=3.0Hz), 5.71–5.85 (m, 1H), 5.08–5.17 (m, 2H), 4.05–4.18 (m, 2H), 2.13–2.43 (m, 2H), 1.71 (s, br, OH, 1H), 1.05–1.30 (m, 3H). |
| 6 | C = 49.69<br>H = 4.60<br>N = 3.16 | $^1$H NMR (d$_6$DMSO) δ 7.81 (d, 2H, J=7.0Hz), 7.60 (d, 2H, J=7.0Hz), 7.50 (s, br, 1H), 7.41, (d, 2H, J=8.0Hz), 7.32 (m, 2H), 7.24 (m, 1H), 7.18 (s, br, 1H), 4.76 (dd, 2H, J=50Hz, 15Hz), 4.36 (t, 1H, J=7.0Hz), 3.33 (s,3H), 1.20–81.34 (m, 3H), 0.79 (d, 3H, J=6.0Hz), 0.46 (d, 3H, J=6.0Hz). |
| 6 | C = 49.39<br>H = 4.57<br>N = 3.16 | $^1$H NMR (CDCl$_3$) δ 7.74 (d, 2H, J=7.0Hz), 7.50 (d, 2H, J=7.0Hz), 7.07–7.47 (m, 3H), 4.03 (m, 2H), 1.56 (s, br, 1H), 0.89–1.56 (m, 10H). |
| 7 | C = 48.01<br>H = 4.51<br>N = 3.35 | $^1$H NMR (CDCl$_3$) δ 7.71–7.80 (m, 2H), 7.31–7.51 (m, 4H), 7.12 (d, 0.5H, J=2.4Hz), 7.22 (d, 0.5H, J=2.4Hz), 4.40–4.56 (m, 1H), 3.71–4.11 (m, 1H), 1.72 (s, br, 1H), 1.11–1.50 (m, 8H). |
| 8 | C = 54.13<br>H = 5.43<br>N = 2.76 | $^1$H NMR (CDCl$_3$) δ 7.69 (d, 2H, J=8.0Hz), 7.44 (d, 2H, J=8.0Hz), 7.31–7.35 (m, 1H), 6.99–7.18 (m, 2H), 4.79–4.81 (m, 1H), 4.46–4.53 (m, 1H), 3.11–3.27 (m, 2H), 1.26–1.66 (m, 6H), 1.13 (d, 3H, J=6.6Hz), 0.83–0.95 (m, 6H) |
| 9 | C = 47.00<br>H = 3.73<br>N = 3.39 | $^1$H NMR (CDCl$_3$) δ 7.53 (d, 2H, J=7.0Hz), 7.08–7.47 (m, 5H), 3.92–4.15 (m, 1H), 3.43–3.59 (m, 1H), 1.82 (s, br, 1H), 1.05–1.30 (m, 6H). |
| 9 | C = 47.03<br>H = 3.78<br>N = 3.34 | $^1$H NMR (CDCl$_3$) δ 7.69 (d, 2H, J=7.0Hz), 7.30–7.51 (m, 4H), 7.08 (d, 1H, J=3Hz), 4.08–4.15 (m, 1H), 3.94–3.97 (m, 1H), 1.54 (s, br, 1H), 1.27–1.23 (m, 6H). |

TABLE 2-continued

| | | |
|---|---|---|
| 10 | C = 49.25<br>H = 4.48<br>N = 3.22 | ¹H NMR (CDCl₃) δ 7.73 (d, 2H, J=7.0Hz), 7.50 (d, 2H, J=7.0Hz), 7.30–7.47 (m, 2H), 7.07 (d, 1H, J=3Hz), 4.21–4.27 (m, 1H), 3.70–3.76 (m, 1H), 1.62–1.72 (m, 1H), 1.52 (s, br, 1H), 0.84–1.11 (m, 9H). |
| 11 | C = 50.39<br>H = 4.78<br>N = 3.13 | ¹H NMR (CDCl₃) δ 7.71 (t, 2H, J=2.0Hz), 7.06–7.50 (m, 5H), 4.19–4.26 (m, 1H) 3.95–4.02 (m, 1H), 1.63–1.72 (m, 1H), 0.88–1.36 (m, 12H). |
| 12 | RT = 1.93 min<br>(M − H)⁻ = 460.09 | ¹H NMR (CDCl₃) δ, 7.03–7.72 (m, 7H), 4.35–4.42 (m, 1H), 4.09–4.23 (m, 1H), 3.90 (t, 1H, J= 8.5Hz), 0.85–1.77 (m, 12H). |
| 13 | C=51.73<br>H = 4.71<br>N = 2.91 | ¹H NMR (CDCl₃) δ, 7.65–7.74 (m, 2H), 7.05–7.51 (m, 5H), 4.22–4.30 (m, 1H), 3.78–3.81 (m, 1H), 0.85–1.85 (m, 15H). |
| 14 | C =54.04<br>H = 4.24<br>N = 2.57 | ¹H NMR (CDCl₃) δ, 7.29–7.81 (m, 11H), 6.67 (d, 0.5H, J=2.5Hz), 5.47–5.51 (m, 1H), 4.04–4.10 (m, 1H), 1.01–1.39 (m, 4H). |
| 15 | RT = 1.77 min<br>(M − H)⁻ = 432.98 | ¹H NMR (CDCl₃) δ, 7.71 (d, 2H, J=5.3Hz), 7.11–7.61 (m, 5H), 4.56–4.70 (m, 1H), 4.18–4.45 (m, 1H), 2.30 (s, br, 1H), 1.67–1.82 (m, 3H), 1.25 (d, 3H, J=7Hz). |
| 15 | C = 50.27<br>H = 3.86<br>N = 2.90 | ¹H NMR (CDCl₃) δ, 7.70 (d, 2H, J=5.3Hz), 7.11–7.56 (m, 5H), 4.56–4.58 (m, 1H), 4.18–4.21 (m, 1H), 3.00 (s, br, 1H), 1.67–1.82 (m, 3H), 1.25 (d, 3H, J=7Hz). |
| 16 | RT = 1.87 min<br>(M − H)⁻ = 512.04 | ¹H NMR (CDCl₃) δ, 7.77 (dd, 2H, J=5.0, 2.8Hz), 7.29–7.51 (m, 4H), 6.71–6.84 (m, 3H), 4.69–5.05 (m, 2H), 2.57 (s, 1.5H), 2.46 (s, 1.5H), 2.21 (s, 3H), 2.02 (s, 3H), 0.84–0.90 (m, 3H). |
| 17 | RT = 1.99 min<br>(M − H)⁻ = 496.11 | ¹H NMR (CDCl₃) δ, 7.05–7.97 (m, 12H), 3.81–4.17 (m, 2H), 2.71–2.88 (m, 4H), 1.70 (s, br, 1H), 1.23 (d, 3H, J=9Hz). |
| 17 | C=55.17<br>H = 4.68<br>N = 2.59 | ¹H NMR (CDCl₃) δ, 7.63 (d, 2H, J=8.0Hz), 7.05–7.44 (m, 10H), 3.81–4.17 (m, 2H), 2.71–2.88 (m, 4H), 1.75 (s, br, 1H), 1.13 (d, 3H, J=6.6Hz). |
| 18 | C = 51.10<br>H = 4.70<br>N = 3.03 | ¹H NMR (CDCl₃) δ 7.69–7.75 (m, 2H), 7.19–7.50 (m, 5H), 5.70–5.85 (m, 1H), 4.91–5.08 (m, 2H), 3.98–4.15 (m, 1H), 3.28–3.49 (m, 1H), 2.07–2.30 (m, 3H), 1.40–1.66 (m, 2H), 1.11 (d, 3H, J=7Hz). |
| 18 | C = 50.76<br>H = 4.30<br>N = 3.12 | ¹H NMR (CDCl₃) δ 7.63–7.69 (m, 2H), 7.28–7.50 (m, 4H), 7.18 (d, 1H, J=2.8Hz), 5.71–5.85 (m, 1H), 5.08–5.17 (m, 2H), 4.05–4.18 (m, 1H), 3.25–3.35 (m, 1H), 2.03–2.43 (m, 2H), 1.69 (s, br, 1H), 1.25–1.49 (m, 2H), 1.29 (d, 3H, J= 7Hz). |
| 19 | C = 49.02<br>H = 4.02<br>N = 3.69 | ¹H NMR (CDCl₃) δ 7.60–7.75 (m, 2H), 7.33–7.60 (m, 3H), 7.05–7.25 (m, 2H), 4.64–4.71 (m, 1H), 2.65–2.70 (m, 1H), 1.77 (s, br, 1H), 1.31 (d, 3H, J=7Hz), 1.06 (d, 3H, J=7.5Hz |
| 19 | C = 48.62<br>H = 4.31<br>N = 3.39 | ¹H NMR (CDCl₃) δ 7.59–7.73 (m, 2H), 7.30–7.60 (m, 4H), 7.08–7.15 (m, 1H), 4.34–4.41 (m, 1H), 3.94–3.97 (m, 1H), 1.97 (s, br, 1H), 1.04–1.23 (m, 6H). |
| 20 | RT = 1.87 min<br>(M − H)⁻ = 430.01 | ¹H NMR (CDCl₃) δ 7.83 (d, 2H, J=8.7Hz), 7.50–7.71 (m, 1H), 7.50 (d, 2H, J=8.0Hz), 7.32–7.39 (m, 1H), 7.08–7.19 (m, 1H), 5.72–5.89 (m, 1H), 4.87–5.11 (m, 2H), 4.00–4.11 (m, 1H), 3.22–3.63 (m, 1H), 1.03–2.30 (m, 8H). |

TABLE 2-continued

| | | | |
|---|---|---|---|
| 20 | | C = 52.66<br>H = 4.56<br>N = 3.06 | $^1$H NMR (CDCl$_3$) δ 7.80 (d, 2H, J=8.0Hz), 7.50–7.71 )m, 1H), 7.32–7.49 (m, 3H, 7.08–7.19 (m, 1H), 5.72–5.89 (m, 1H), 4.83–5.10 (m, 2H), 3.91–4.08(m, 1H), 3.22–3.63 (m, 1H), 1.10–2.21 (m, 8H). |
| 21 | | C = 51.60<br>H = 4.13<br>N = 3.33 | $^1$H NMR (CDCl$_3$) δ, 7.73 (d, 2H, J=7.0Hz), 7.48 (d, 2H, J=6.8Hz), 7.30–7.36 (m, 1H), 7.03–7.10 (m, 2H), 4.26–4.58 (m, 2H), 2..04 (s, br, 1H), 1.57–1.79 (m, 3H), 1.00–1.23 (m, 3H). |
| 21 | | RT = 1.71 min<br>(M − H)$^-$ =<br>414.03 | $^1$H NMR (CDCl$_3$) δ, 7.73 (d, 2H, J=6.0Hz), 7.46 (d, 2H, J=8.0Hz), 7.30–7.38 (m, 1H), 7.02–7.11 (m, 2H), 4.30–4.55 (m, 2H), 3.01 (s, br, 1H), 1.54–1.92 (m, 3H), 1.01–1.11 (m, 3H). |
| 22 | | C = 54.84<br>H = 4.10<br>N = 2.55 | $^1$H NMR (CDCl$_3$) δ 7.60–7.75 (m, 3H), 7.48 (d, 2H, J=8.0Hz), 7.02–7.32 (m, 4H), 6.86 (d, 2H, J=6.0Hz), 6.77 (m, 1H), 5.20–5.30 (m, 1H), 4.03–4.34 (m, 2H), 3.79 (s, 3H), 1.59 (s, br, 1H), 1.03–1.28 (m, 3H). |
| 23 | | C = 51.89<br>H = 4.31<br>N = 3.30 | $^1$H NMR (CDCl$_3$) δ 7.73 (d, 2H, J=8.5Hz), 7.45 (d, 2H, J=8.5Hz), 7.34–7.38 (m, 1H), 7.05–7.11 (m, 2H), 5.78–5.92 (m, 1H), 5.02–5.17 (m, 2H), 4.04–4.17 (m, 1H), 3.30–3.39 (m, 1H) 2.04–2.44 (m, 2H), 0.93–1.15 (m, 3H). |
| 24 | | C = 45.38<br>H = 3.83<br>N = 2.89 | $^1$H NMR (CDCl$_3$) δ 7.67 (d, 2H, J=8.2Hz), 7.48 (d, 2H, J=8.5Hz), 7.33–7.38 (m, 1H), 7.06–7.12 (m, 2H), 4.20–4.29) (m, 2H), 3.82–3.93 (m, 1H), 2.89–3.06 (m, 1H), 2.61–2.70 (m, 1H), 1.27 (d, 3H, 6.0Hz). |
| 25 | | C = 55.72<br>H = 5.26<br>N = 3.00 | $^1$H NMR (CDCl$_3$) δ 7.66 (d, 2H, J=8.0Hz), 7.52 (d, 2H, J=8.0Hz), 7.32–7.41 (m, 1H), 6.99–7.18 (m, 2H), 4.77–4.79 (m, 1H), 4.59–4.61 (m, 1H), 3.23–3.39 (m, 1H), 1.26–1.86 (m, 12H), 1.13–1.25 9m, 3H), 0.95–1.00 (m, 3H). |
| 26 | | | |
| 27 | | C = 51.27<br>H = 4.74<br>N = 3.25 | $^1$H NMR (CDCl$_3$) δ 7.71 (d, 2H, J=8.5Hz), 7.47–(d, 2H, J=8.5Hz), 7.34–7.39 (m, 1H), 6.89–7.11 (m, 2H), 4.00–4.19 (m, 1H), 3.21–3.23 (m, 1H), 1.06–1.52 (m, 5H), 0.93 (d, 3H, 6.0Hz). |
| 28 | | RT = 1.69 min<br>(M − H)$^-$ =<br>461.9 | $^1$H NMR (CDCl$_3$) δ 7.71–7.77 (m, 2H), 7.30–7.53 (m, 4H), 6.95 (d, 1H, J=2.5Hz) 4.46–4.53 (m, 1H), 3.62–4.13 (m, 3H), 1.77–1.88 (m, 1H), 1.42–1.61 (m, 9H) 0.93–1.23 (m, 3H). |
| 29 | | C = 51.51<br>H = 4.99<br>N = 2.96 | $^1$H NMR (CDCl$_3$) δ 7.71–7.80 (m, 2H), 7.30–7.54 (m, 5H), 5.74–5.86 (m, 1H), 4.94–5.12 (m, 2H), 4.16–4.58 (m, 2H), 3.54–3.61 (m, 1H), 1.99–2.35 (m, 3H), 1.48–1.59 (m, 1H), 1.09–1.44 (m, 5H). |
| 30 | | C = 54.82<br>H = 4.19<br>N = 3.13 | $^1$H NMR (CDCl$_3$) δ 7.72–7.82 (m, 4H), 7.29–7.54 (m, 8H), 4.52–4.75 (m, 1H), 4.19–4.48 (m, 1H), 2.22–2.36 (m, 1H), 1.46–1.65 (m, 2H), 1.16–1.28 (m, 3H). |

·A and B denote elution order of diastereomers; a diastereomeric mixture has no designation
·As a 4:1 mixture of Isomer B to A
Note 1, RT=Retention time; HPLC conditions, 3 X 50 mm ODS-A C-18 column, 5 mL/min, 0–100% MeOH/H2O 0.1% TFA 2 min grad

The invention claimed is:

1. A compound of Formula I including its stereoisomers, pharmaceutically acceptable salts, and hydrates thereof,

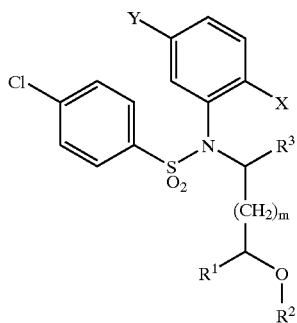

I where:

X and Y are independently selected from halogen, hydroxymethyl, and acetoxymethyl;

$R^1$ is selected from $C_{1-6}$alkyl, $C_{3-6}$alkenyl, $C_{3-6}$alkynyl, $C_{3-7}$cycloalkyl, $C_{5-7}$cycloalkenyl, —$(CH_2)_{1-6}CO_2R^3$, and

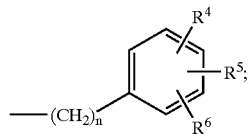

$R^2$ is selected from hydrogen, $C_{1-6}$alkylcarbonyl, $C_{3-7}$cycloalkylcarbonyl, $CONHR^3$, and

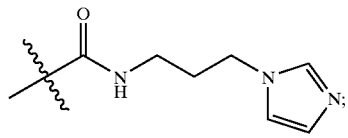

$R^3$ is selected from hydrogen and $C_{1-6}$alkyl;

$R^4$, $R^5$, and $R^6$ are independently selected from hydrogen, $C_{1-6}$alkyl, and $C_{1-6}$alkoxy;

m is 0 or an integer from 1 to 6; and n is 0 or an integer from 1 to 6.

2. A compound of claim 1 wherein $R^3$ is methyl, the carbon to which $R^3$ is attached is of the (R) configuration, and m is 0.

3. A compound of claim 1 where $R^1$ is $C_{1-6}$alkyl, $C_{3-6}$alkenyl, or $C_{3-6}$alkynyl.

4. A compound of claim 2 where $R^1$ is $C_{1-6}$alkyl, $C_{3-6}$alkenyl, or $C_{3-6}$alkynyl.

5. A compound of claim 2 selected from the following group:

N-(2,5-dichlorophenyl)-N-(4-hydroxy-1-hexyn-5-yl)-4-chlorobenzenesulfonamide;

N-(2-fluoro-5-chlorophenyl)-N-(4-hydroxy-1-hexyn-5-yl)-4-chlorobenzenesulfonamide;

N-(2-fluoro-5-chlorophenyl)-N-(4-hydroxy-1-hexen-5-yl)-4-chlorobenzenesulfonamide;

N-(2-fluoro-5-chlorophenyl)-N-(3-hydroxyhex-2-yl)-4-chlorobenzenesulfonamide; and N-(2-hydroxymethyl-5-chlorophenyl)-N-(2-(N-3-(1-imidazolyl)prop-1-ylcarbamoyl)but-3-yl) -4-chlorobenzenesulfonamide.

6. A compound of claim 1 wherein $R^3$ is methyl, the carbon to which $R^3$ is attached is of the (R) configuration, and m is 1.

* * * * *